US006217538B1

(12) United States Patent
Anderson

(10) Patent No.: US 6,217,538 B1
(45) Date of Patent: Apr. 17, 2001

(54) CERVICAL/UPPER THORACIC RELAXER

(76) Inventor: Mark A. Anderson, 303 Henry M. Chandler Dr., Rockwall, TX (US) 75032

(*) Notice: Subject to any disclaimer, the term of this patent is extended or adjusted under 35 U.S.C. 154(b) by 0 days.

(21) Appl. No.: 09/257,222

(22) Filed: Feb. 25, 1999

(51) Int. Cl.[7] ........ A61F 5/00

(52) U.S. Cl. ........ 602/35; 602/33

(58) Field of Search ........ 602/33, 32, 34, 602/35, 36, 38; 5/633, 634, 636, 637, 630, 610; 297/350, 352, 377, 354.11, 354.12, 354.13, 380, 42, 45; 606/237, 238, 240–245; 248/166, 436, 173; 24/493

(56) References Cited

U.S. PATENT DOCUMENTS

| | | | | |
|---|---|---|---|---|
| Re. 32,791 | | 11/1988 | Saunders . | |
| 74,786 | * | 2/1868 | Annis | 5/634 |
| D. 282,803 | * | 3/1986 | Righini | 5/636 |
| 649,300 | * | 5/1900 | Hall et al. | 248/166 |
| 858,908 | * | 7/1907 | Rauch | 5/634 |
| 3,565,419 | * | 2/1971 | Allard | 297/377 |
| 3,675,646 | | 7/1972 | Corcoran . | |
| 3,847,335 | * | 11/1974 | Ross | 248/166 |
| 4,166,459 | | 9/1979 | Nightingale . | |
| 4,266,759 | * | 5/1981 | Liebman | 269/323 |
| 4,524,763 | * | 6/1985 | Eberling, Jr. | 606/241 |
| 4,534,341 | * | 8/1985 | Bart et al. | 606/241 |
| 4,596,384 | * | 6/1986 | Blosser | 5/465 |
| 4,715,650 | * | 12/1987 | Berman et al. | 297/350 |
| 4,724,828 | | 2/1988 | Barnes et al. . | |
| 4,736,736 | | 4/1988 | Moers et al. . | |
| 4,760,842 | | 8/1988 | Holmes . | |
| 4,775,182 | * | 10/1988 | Von Hoffman | 297/350 |
| 4,922,894 | | 5/1990 | Gipson et al. . | |
| 5,067,483 | | 11/1991 | Freed . | |
| 5,147,287 | | 9/1992 | Jewell et al. . | |
| 5,341,517 | * | 8/1994 | Bly | 4/236 |
| 5,348,385 | * | 9/1994 | Berg | 248/243 |
| 5,411,471 | | 5/1995 | Terrazas . | |
| 5,484,393 | * | 1/1996 | McCoy | 602/33 |
| 5,542,910 | | 8/1996 | Oliver . | |
| 5,569,175 | | 10/1996 | Chitwood . | |
| 5,575,295 | | 11/1996 | Khalsa et al. . | |
| 5,662,597 | * | 9/1997 | Chitwood | 602/32 |
| 5,709,649 | | 1/1998 | Chitwood . | |
| 5,897,167 | * | 4/1999 | Keith | 297/397 |
| 5,921,627 | * | 7/1999 | Risetter | 297/354.13 |
| 5,921,901 | * | 7/1999 | Palacios | 482/142 |
| 5,991,651 | * | 11/1999 | LaBarbera | 5/622 |

* cited by examiner

*Primary Examiner*—Mickey Yu
*Assistant Examiner*—Justine R. Yu
(74) *Attorney, Agent, or Firm*—Dennis T. Griggs

(57) ABSTRACT

A portable, free-standing head support frame for passively inducing cervical and thoracic flexion while maintaining traction includes a base support platform for placement on the floor or other stable treatment surface, an upright head support frame that projects transversely with respect to the base platform, a head cradle including a V-shaped occipital engagement block with engagement edges extending transversely on opposite sides of the occipital center line, a strap to immobilize the patient's head, and an adjustable coupling for holding the head cradle at a desired elevation above the base platform. The patient assumes a static, semi-reclined position with the patient's upper torso and head being elevated and inclined with respect to the support surface. The weight of the patient's upper torso induces a gentle stretch and traction in cervical and thoracic flexion, providing relief of cervical and upper thoracic muscle spasm, and facet joint, costovertebral joint and soft tissue conditions. The principal component parts of the frame are pivotally coupled so that the support frame is erectable to an upright, stable treatment position for accommodating therapy, and is completely foldable and collapsible to a minimum profile position for storage, without requiring tools.

6 Claims, 8 Drawing Sheets

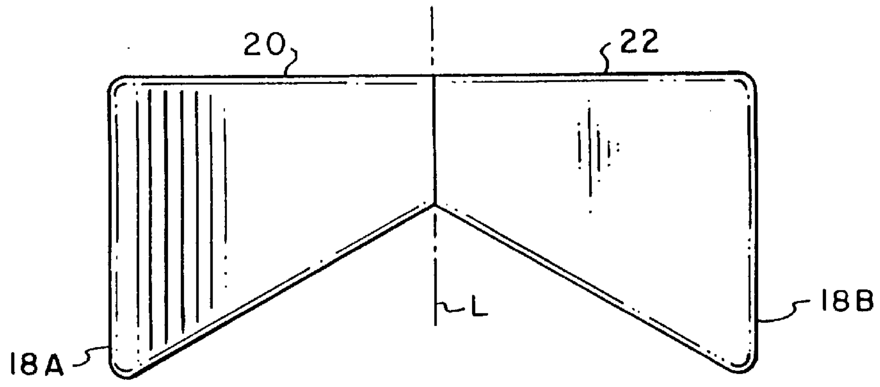
FIG. 5
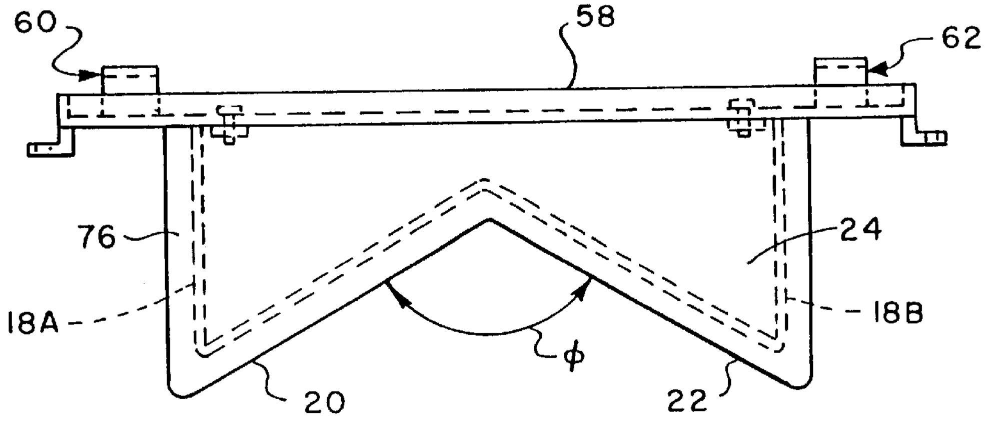
FIG. 6
FIG. 7
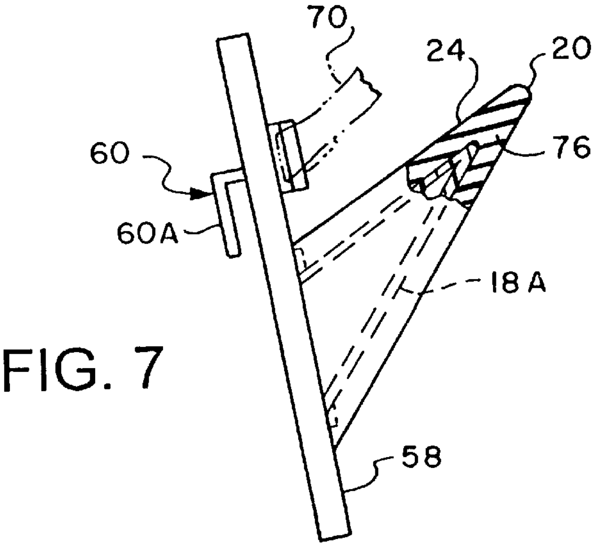

CERVICAL/UPPER THORACIC RELAXER

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

This invention relates generally to passive cervical traction devices, and in particular to gravity-assisted occipital support and cervical stretching apparatus used during the administration of physical therapy.

Spinal cervical and thoracic disorders can result from trauma or from long-term life-style activities, or emotional stress. These conditions can cause cervical muscle tension/spasm, facet joint locking, ligament/capsule tightness and contracture, soft-tissue hypomobilities and arthritis. Conventional therapies include traction, manipulation, mobilization, therapeutic exercise, heat/cold therapy, ultrasound and short-wave diathermy.

In one physical therapy treatment protocol, the patient rests in a semi-reclined position on a treatment table while cervical and thoracic flexion is applied manually by a physical therapist. During this procedure, the therapist's hands (the heels of his hands) engage the patient's occiput bilaterally, providing slight cervical/thoracic traction and stretch. The therapist rests his elbows in a slightly spread position on the treatment surface directly behind the patient's head. This technique has proven to be effective, but requires one-on-one attendance by a therapist. Additionally, it imposes a physical strain on the therapist, who is required to maintain his/her arms and hands in a spread apart, fixed position during the treatment session, which extends over a typical treatment period of five minutes.

Conventional traction devices can be categorized as clinical machines and home units. Typically, clinical machines are powered by electric, pneumatic or hydraulic means, and are used in the supine position. Home devices are used in either the supine or seated position (utilizing standard chairs found in the home such as a folding chair or kitchen chair) and are usually passive, usually relying on a suspended weight in one form or another.

Portable cervical traction devices have been developed as an aid to the therapist to provide for home treatment. These mechanical devices employ passive (gravity-assisted) supports for inducing a traction effect at the intervertebral joints (facet and/or disc) and stretching the patient's neck muscles, ligaments and other supporting tissues.

Conventional therapy devices include cervical traction machines which either require or avoid transmission of forces through the left and right temporomandibular joints (TMJ). One cervical traction machine utilizes a recliner chair with a head harness for achieving a desired degree of cervical or thoracic flexion while the patient is seated. The head harness used in most home traction kits require the transmission of force through the TMJ, which can be painful.

Other traction devices such as the Saunders cervical traction machine (U.S. Pat. No. Re. 32,791) includes adjustable wedges which avoid force through the TMJ. The flexion angle of the neck can be adjusted from 15°–25° in the supine position. However, the Saunders home device cannot be adjusted to include thoracic flexion and is relatively expensive.

Presently, there is no conventional device or appliance that is as effective as the manual treatment provided by a trained professional. One reason for this is the ability of the trained professional to continuously modify and adjust the manually applied stretch and traction force in response to feedback information received from the patient as the therapy progresses. Nevertheless, a need exists for a passive device which can be used by the therapist as an adjunct to manual treatment protocols. Moreover, a need also exists for a portable apparatus that can be used safely and effectively by a patient at home on an unsupervised outpatient basis during self-administered therapy for the relief of pain and muscle spasm reduction.

BRIEF SUMMARY OF THE INVENTION

The present invention provides a portable, free-standing support frame for passively inducing cervical and thoracic flexion while maintaining traction. The patient assumes a static, semi-reclined position with the patient's upper torso and head being elevated and inclined with respect to the floor or other support surface. The support apparatus includes a free-standing frame with a base platform for placement on a floor or other stable surface, a head support frame that projects transversely with respect to the base platform and a head cradle with a V-shaped engagement block including edge portions extending transversely on opposite sides of the occipital center line for engaging the occiput. The head cradle is adjustably coupled to the head frame for holding the engagement block at a selected elevation above the base platform, which is determined by the length of the patient's torso.

According to this technique, most of the patient's body weight is supported by the floor or other support surface, with the weight of the patient's upper torso providing a gentle stretch/traction force maintained in cervical and thoracic flexion. The edge portions of the V-shaped engagement block of the head cradle are symmetrically arranged and slope away from the occipital center line to accommodate a wide range of head sizes.

The occipital engagement cradle can be quickly set-up, adjusted and supported at a desired elevation for maintaining a gentle, gravity-assisted cervical and thoracic flexion stretch/traction. After the initial set-up, the traction forces and flexion angle are adjusted by positioning the patient's pelvis and lower extremities away from or closer to the cradle. A therapeutic effect is produced by combining gravity with the angle of flexion along the cervical and thoracic spine, which results in the mild traction of intervertebral joints, muscle relaxation, and stretch of hypomobile tissues throughout the treatment region when performed statically.

The foregoing gravity-assisted, passive features are provided by the portable, free-standing support frame of the present invention which can be quickly erected to a stable, operative position for therapy. Its principal component parts are pivotally coupled so that it is expandable into the stable, upright service position and completely foldable and collapsible to a minimum profile configuration for storage, without requiring tools for set-up or conversion to the storage configuration.

BRIEF DESCRIPTION OF THE DRAWING

The accompanying drawing is incorporated into and forms a part of the specification to illustrate the preferred embodiments of the present invention. Various advantages and features of the invention will be understood from the following detailed description taken in connection with the appended claims and with reference to the attached drawing figures in which:

FIG. 5 is a front elevational view of the occipital support cradle;

FIG. 6 is a top plan view of the occipital support cradle mounted on a coupling plate;

FIG. 7 is a left side elevational view thereof, shown partly in section;

DETAILED DESCRIPTION OF THE INVENTION

Figure 1:
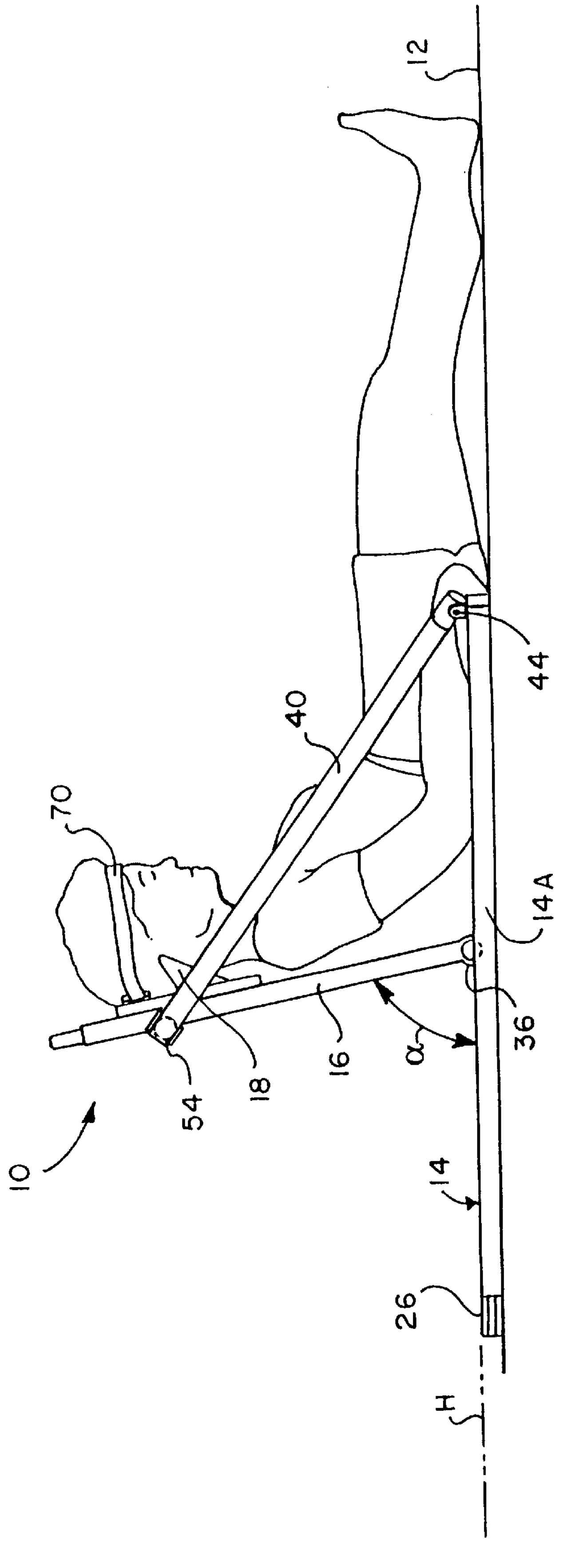
FIG. 1 is side elevational view of the device and its occipital support cradle in the operative treatment position with a patient utilizing the apparatus for passive flexion stretch and traction.

Preferred embodiments of the invention will now be described with reference to various examples of how the invention can best be made and used. Like reference numerals are used throughout the description and several views of the drawing to indicate like or corresponding parts.

Figure 2:
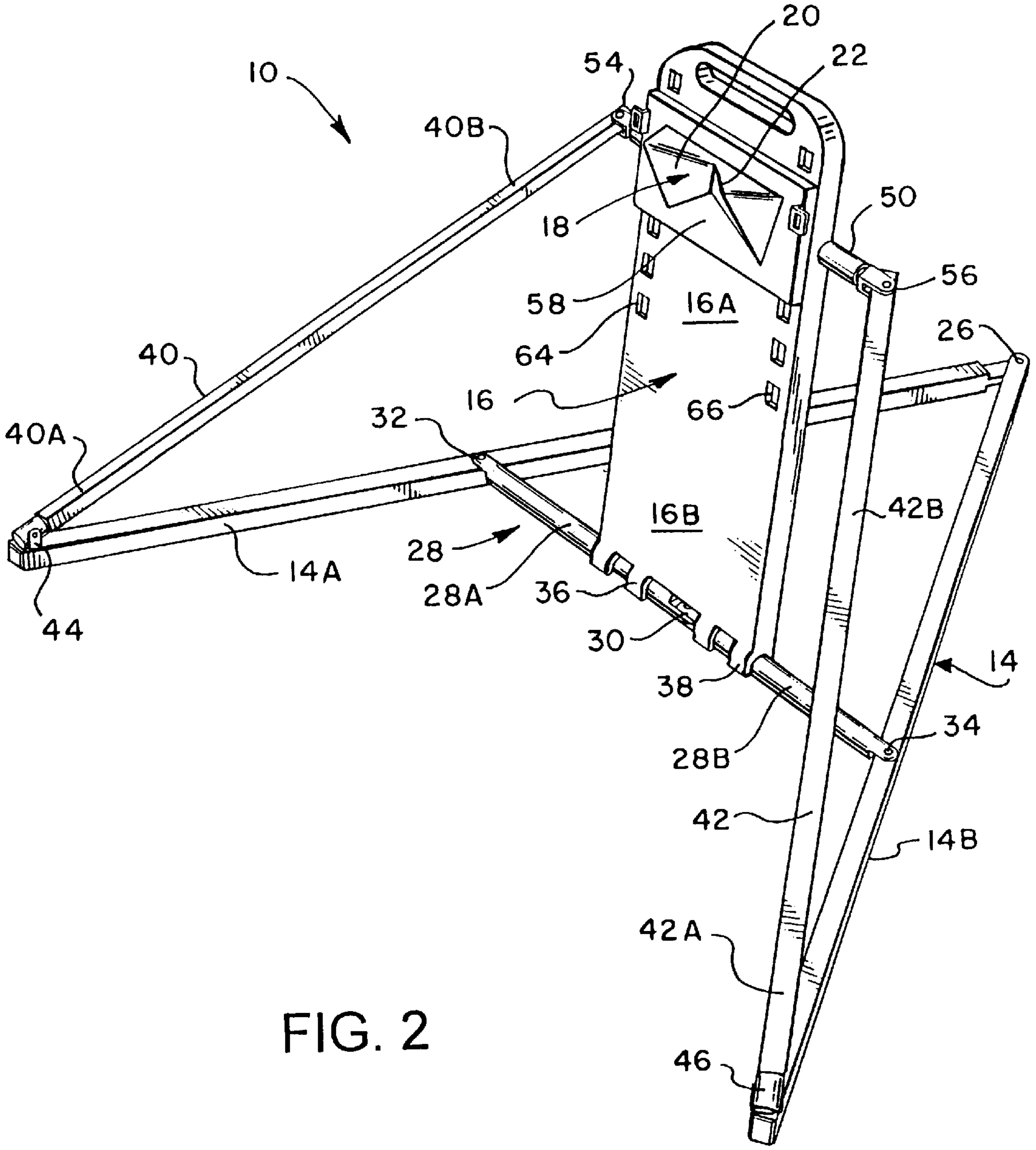
FIG. 2 is a front perspective view thereof.

Referring initially to FIG. 1 and FIG. 2, a portable, free-standing support frame assembly 10 is shown in its erect, upright treatment position for maintaining a gentle stretch, traction force in cervical and thoracic flexion. A patient assumes a static, semi-reclined position (FIG. 1) with patient's upper torso and head being elevated and inclined with respect to the floor or other support surface 12. The support frame assembly 10 includes a base platform 14 for flat engagement on the floor surface 12. A head support frame in the preferred form of a bolster board 16 projects transversely with respect to the base platform in the erect, upright treatment position. Preferably, the bolster board 16 is inclined at an angle $\alpha$ in the range of 75°–90° with respect to the base platform when the support frame assembly 10 is erected in the upright treatment position.

A head cradle in the preferred form of a V-shaped occipital engagement block 18 is releasably mounted on the head support frame, so that its elevation above the floor surface 12 can be manually adjusted. The V-shaped occipital engagement block 18 includes edge portions 20, 22 that extend transversely on opposite sides of the occipital center line L (FIG. 5 and FIG. 10) for engaging the occiput. The head cradle 18 is set so that the patient's head is positioned at a selected elevation above the floor surface 12, which is determined by length of the patient's torso.

Figures 8, 9:
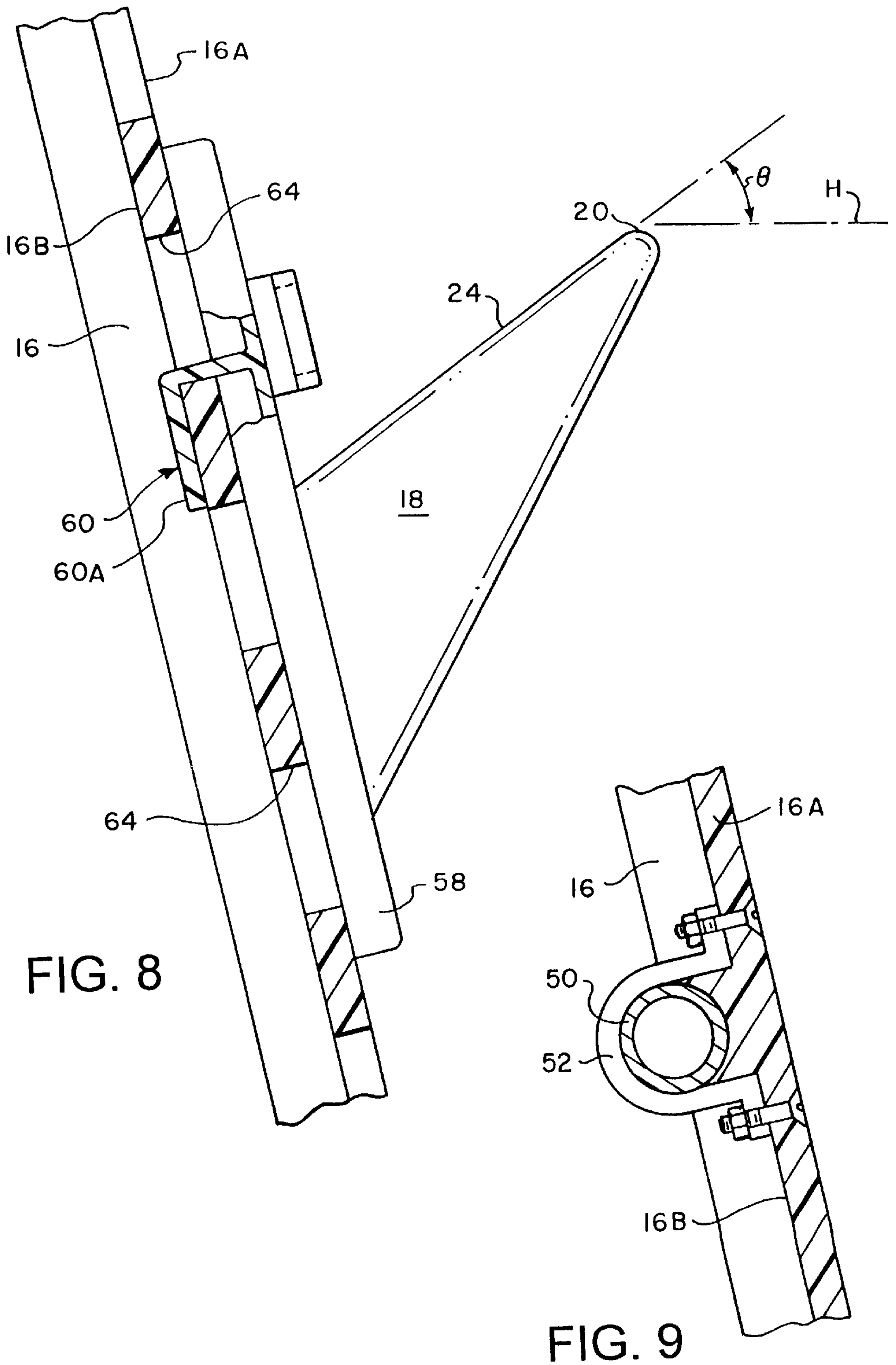
FIG. 8 is a side elevational view, partly in section, of the occipital support assembly mounted on a support platform.
FIG. 9 is a sectional view, partially broken away, of a rotatable coupling.

The edge portions 20, 22 extend outwardly from a vertex point and define an included angle $\phi$ (FIG. 6) in the range of 90°–110°. The head cradle 18 also includes a flat ledge surface 24 which slopes at an angle $\theta$ with respect to a horizontal line H (which is parallel with the base platform 14), as shown in FIG. 8. According to this arrangement, the edge portions 20, 22 are presented for bilateral engagement against the underside of the occipital lobes. The base support platform includes left and right base rails 14A, 14B that are joined together by a pivot coupling 26, thereby permitting folding movement of the left base rail relative to the right base rail from a retracted minimum profile position (FIG. 12) to a spread-apart operative support position, as shown in FIG. 2.

The base rails 14A, 14B are stabilized in the spread-apart, operative support position by a foldable cross-bar assembly 28 that extends between the left and right base rails in the spread-apart, operative position. The cross-bar assembly 28 includes first and second cross-bar segments 28A, 28B that are joined together by a pivot coupling 30 which permits folding movement of the cross-bar segments relative to each other. The opposite ends of the cross-bar segments are joined to the base rails 14A, 14B by pivot couplings 32, 34, respectively.

Figure 12:
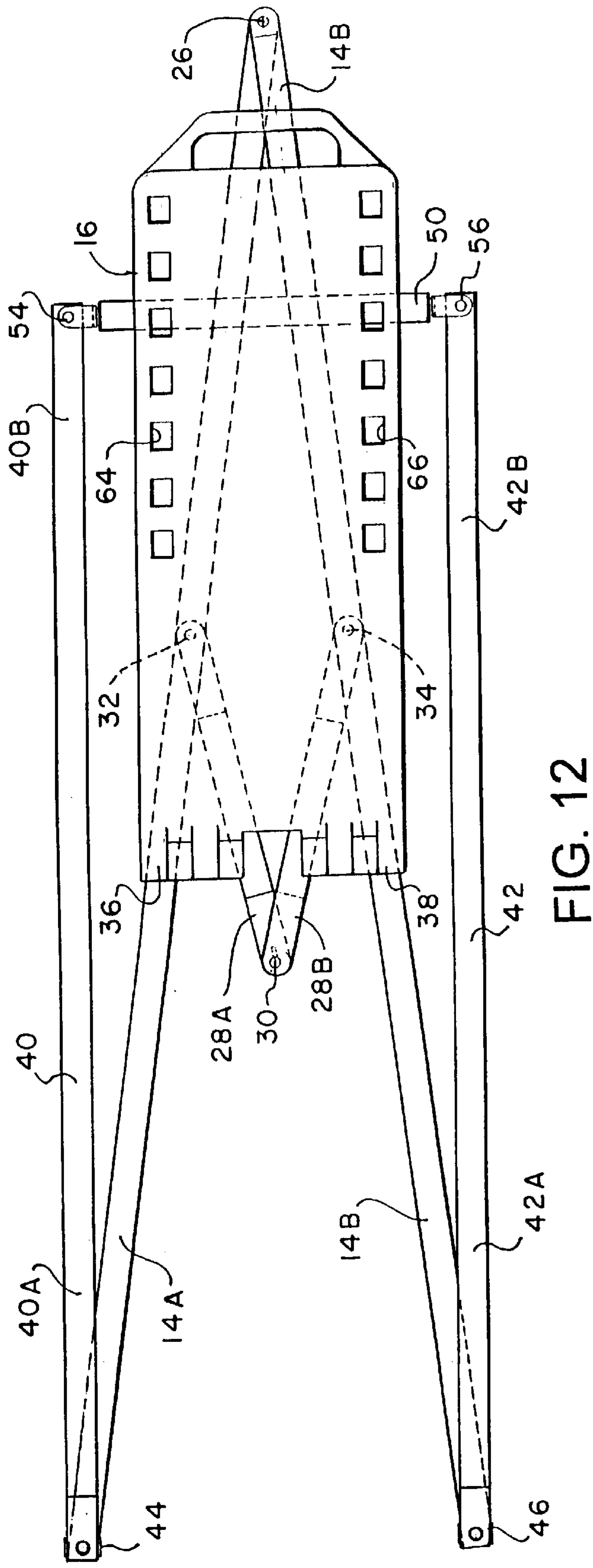
FIG. 12 is a top plan view of the traction apparatus shown in its collapsed, minimum profile storage configuration; and, FIG. 13 is a side elevational view thereof.
Figure 13:
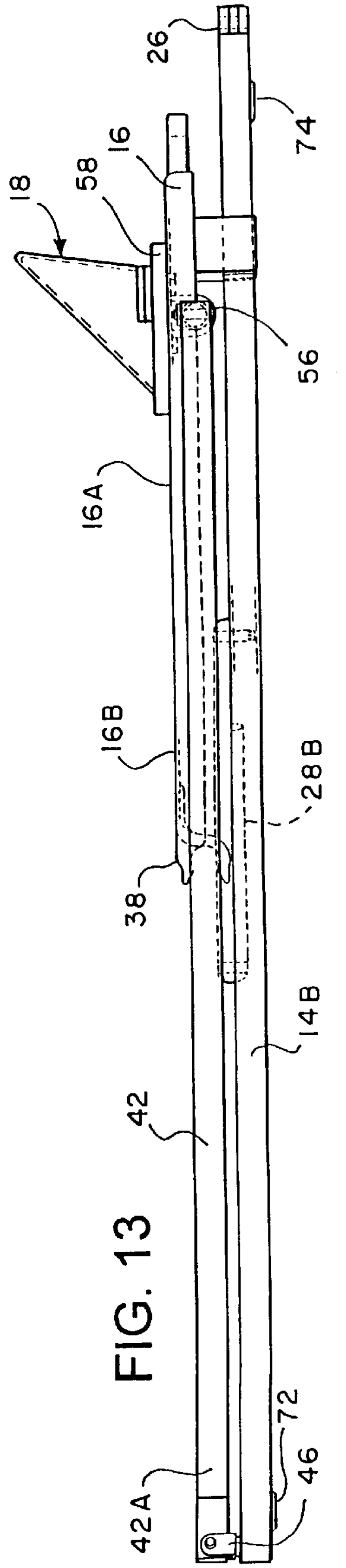

The extended position of the cross-bar segments is stabilized by the clamping attachment of the bolster board 16. The base end portion 16B of the bolster board 16 is fitted with open ended clamps 36, 38 which in combination with the bolster board 16 form a bridge across the pivot coupling 30, thereby securely locking the cross-bar segments 28A, 28B in the fully extended position. The clamps 36, 38 resiliently engage the cross-bar segments, thus permitting the bolster board 16 to rotate in pivotal movement about the cross-bar assembly during erection of the support frame assembly. Additionally, the clamps 36, 38 can be separated from the cross-bar assembly to permit folding movement to the minimum profile configuration as shown in FIG. 12 and FIG. 13.

Figure 4:
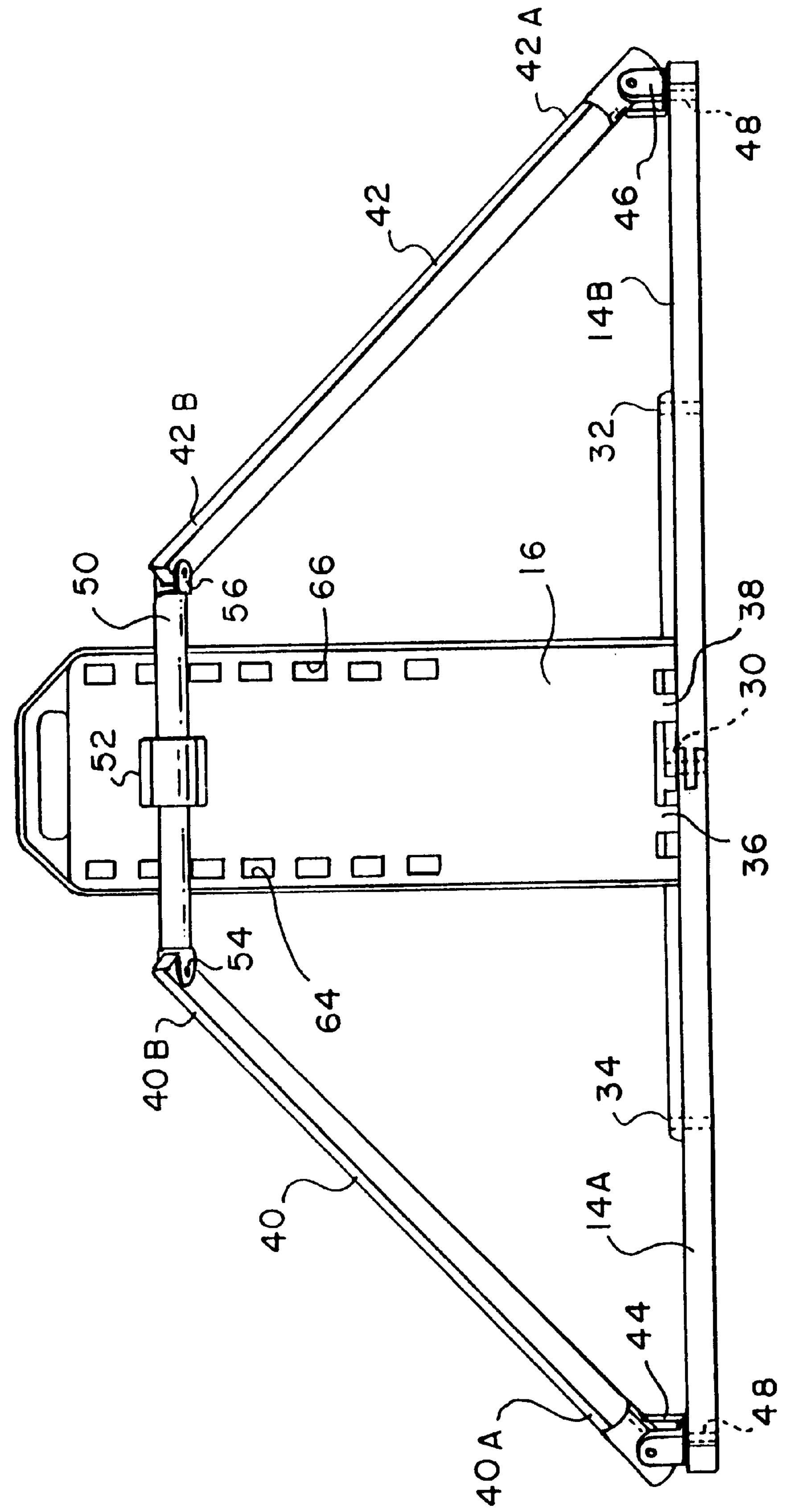
FIG. 4 is a rear perspective view thereof.
Figure 11:
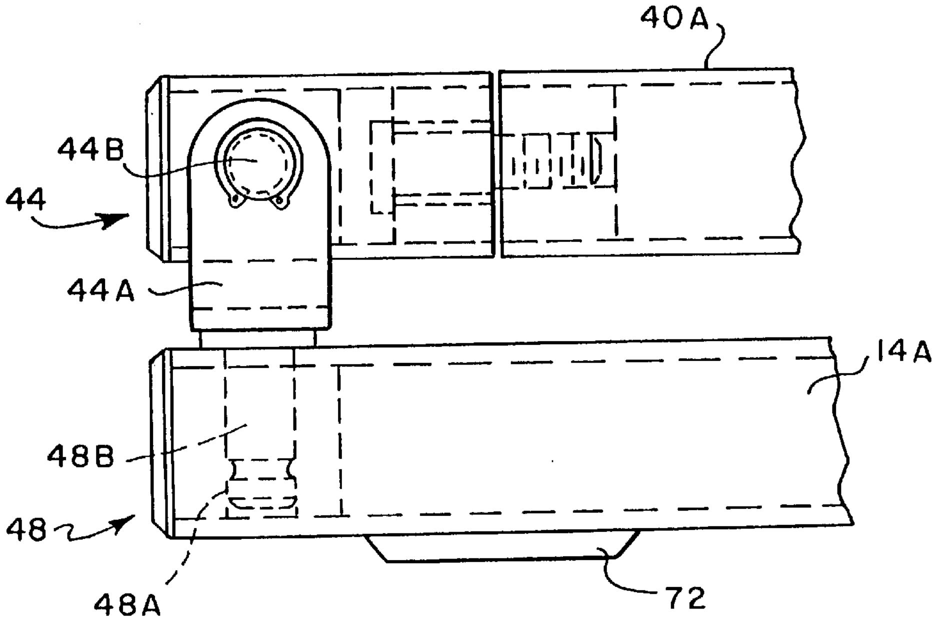
FIG. 11 is an elevational view, partially in section, showing a pivotal coupling and non-skid pad.

Referring now to FIG. 2 and FIG. 4, the bolster board 16 is stabilized in the upright operative position by left and right struts 40, 42. A pair of pivotal coupling members 44, 46 connect the struts to the base rails 14A, 14B, thereby permitting folding movement of the struts relative to the base rails. Additionally, the pivot couplings 44, 46 are further rotatably coupled to the base rails 14A, 14B by a swivel cooupling 48. In the preferred embodiment, each pivotal coupling member 44, 46 includes a clevis 44A and pivot pin 44B (FIG. 11). The swivel coupling preferably is formed by a ball and socket union 48A, 48B.

The opposite ends of the struts 40, 42 are pivotally coupled to the bolster board 16 by an upper cross-bar 50. The cross-bar 50 is secured to the bolster board 16 by a compression clamp 52. Referring to FIG. 4 and FIG. 9, the tightness of the compression fit between the clamp 52 and the cross-bar 50 is adjusted so that the bolster board 16 can be manually rotated as required during set-up.

The upper end portions 40B, 42B of the struts are pivotally joined to the cross-bar 50 by pivot couplings 54, 56, respectively.

Figure 3:
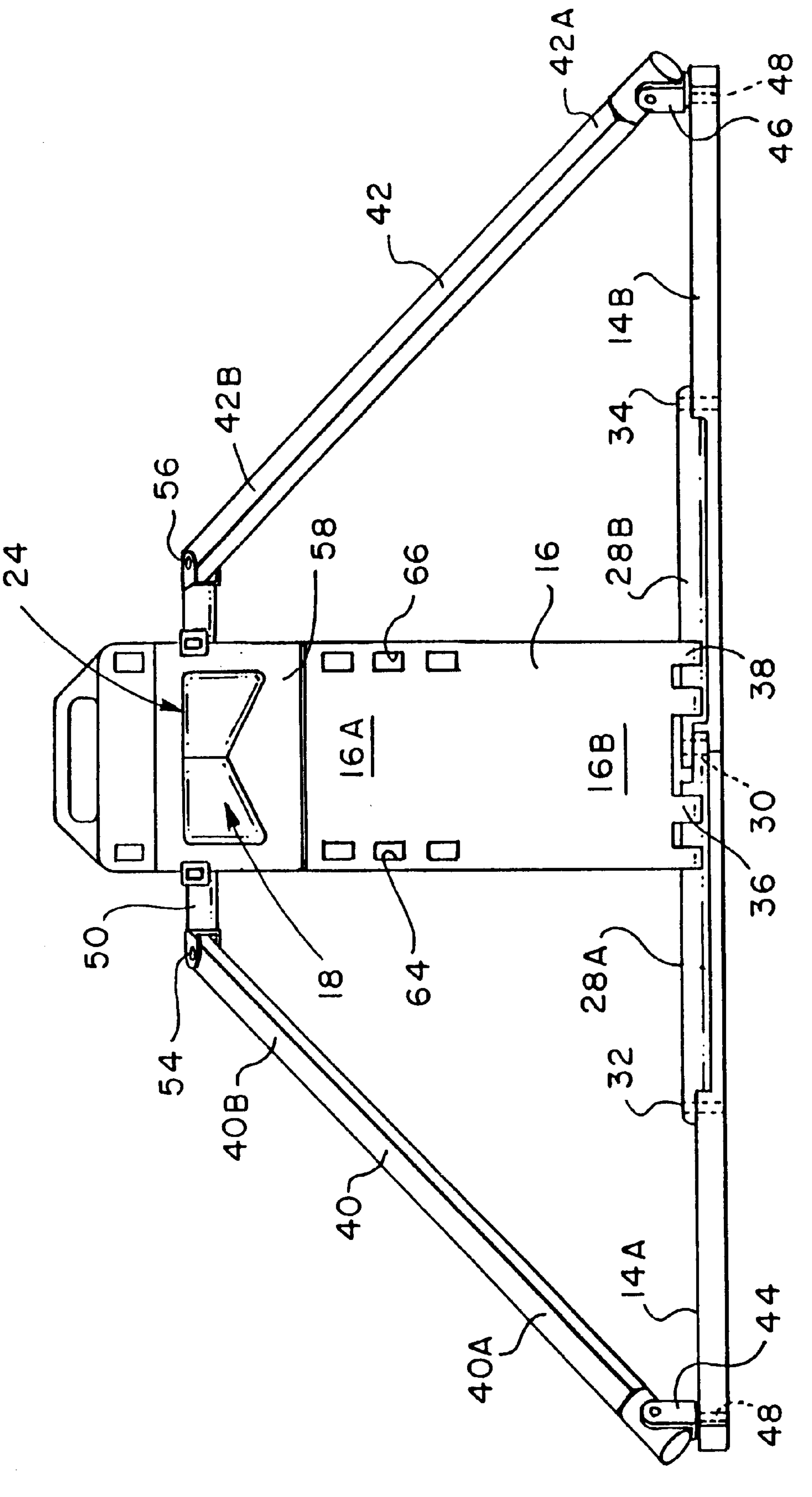
FIG. 3 is a front elevational view thereof.
Figure 10:
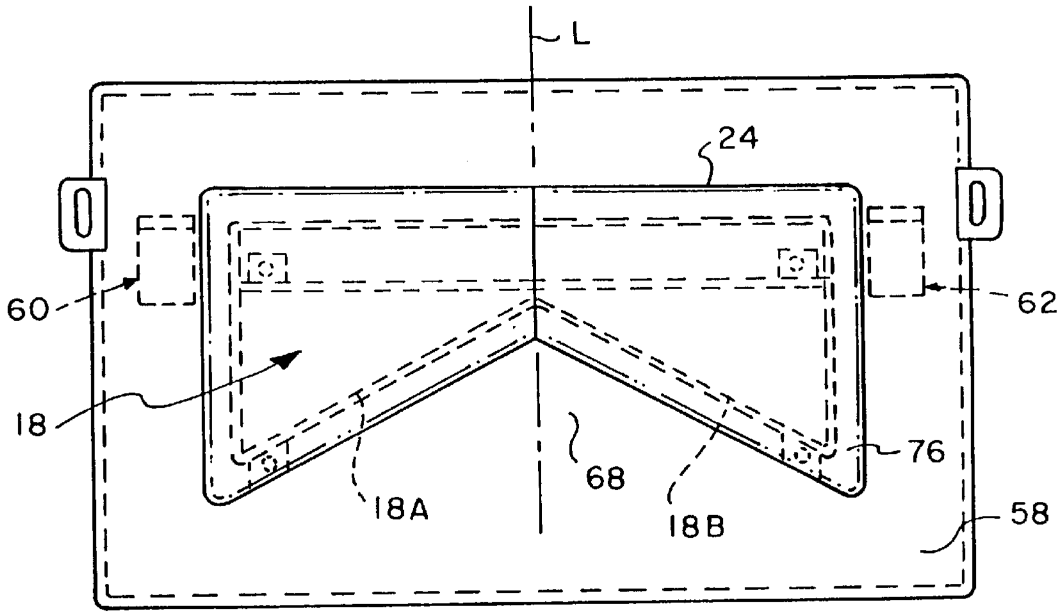
FIG. 10 is a front plan view of the coupling plate and occipital support cradle.

Because of the variation of physical body size from patient-to-patient, it is necessary to provide means for adjusting the elevation of the head support cradle 18 with respect to the floor surface. According to a preferred embodiment of the present invention, adjustment of the head support cradle 18 is provided by a coupling plate 58 which is releasably attached to the bolster board 16 by a pair of L-shaped brackets 60, 62 (FIG. 8 and FIG. 10). Each L-shaped bracket includes a right angle tang portion 60A, 62A, respectively, which is engagable with the reverse side 16B of the bolster board as shown in FIG. 8. In this arrangement, the bolster board is intersected by multiple pairs of index slots 64, 68. The slots of each pair are in horizontal alignment with each other, and the slots are arranged in two parallel columns, with the slots within each column being in vertical alignment as shown in FIG. 3 and FIG. 4.

Referring now to FIG. 5, FIG. 6, FIG. 7, FIG. 8 and FIG. 10, the occipital support cradle 18 is generally in the form of a V-shaped wedge with left and right occipital support block portions 18A, 18B diverging symmetrically from the occipital center line L. As shown in FIG. 5, the left and right block portions 18A, 18B form sidewall boundaries of a pocket which receives the patient's neck, as shown in FIG. 1.

According to this arrangement, the patient's head is supported against the coupling plate, with the occipital lobes engaged against the edge portions 20, 22. Preferably, the pocket 68 is deep enough so that the patient's neck and the patient's shoulders do not touch the bolster board when the patient is correctly positioned. This allows the patient to apply his torso weight for inducing a gentle flexion stretch/ mild traction force, assisted only by gravity. Moreover, the patient can rotate his torso to either side while his head and neck remain engaged and immobilized. Preferably, the patient's head is secured by a strap 70 to ensure that the proper engagement is maintained. To further assure stable positioning of the support assembly 10, non-skid pads 72, 74 are attached to the underside of the left and right base rails 14A, 14B (FIG. 11 and FIG. 13). Preferably, the occipital support blocks 18A, 18B are enclosed within a soft, disposable covering 76, either a vinyl or foam material.

During set-up of the portable support frame 10, the base rails 14A, 14B, the cross-bar segments 28A, 28B and the struts 40, 42 are unfolded outwardly with respect to each other to the fully extended position as shown in FIG. 2. Referring to FIG. 12, which shows the collapsed, minimum profile condition, set-up is initiated by unfolding and extending the base rails 14A, 14B simultaneously with unfolding extension movement of the struts 40, 42. At the same time, the lower cross-bar assembly 28 is unfolded to the straight line support position which limits further unfolding movement of the base rails. Next, the bolster board 16 is rotated downwardly, until the clamps 36, 38 are in a position to engage the cross-bar 28. The cross-bar segments 28A, 28B are then inserted into the jaws of the resilient clamps 36, 38, which form a snap-fit compression union. The struts, base rails and bolster board are dimensioned appropriately to position the bolster board within the preferred angular range.

The portable support frame 10 of the present invention provides the following advantages:

1. It combines cervical and thoracic flexion in order to produce a mild flexion stretch of the posterior soft tissues, including muscles, ligaments and facet capsules.
2. It combines this flexion stretch with a static traction of the weight bearing intervertebral joints.
3. The amount of traction force is determined and adjusted by the user changing his or her body position.

My invention cannot be used for conventional intermittent or static traction for several reasons. Chief amoung them is that the amount of force for the "pull" cannot be precisely controlled (important when applying traction). The therapist must know the amount of force in order to objectively treat certain conditions, as well as make knowledgeable changes based on patient response during or following the prior treatment.

Another key distinguishing feature is that a conventional traction device is often used to treat a bulging intervertebral disc. The angle of pull force can be critical, and the bulge is almost always in the cervical region. Clinical and home traction devices allow the angle of pull to be adjusted in accordance with the faulty disc. My support frame invention does not have this adjustability, and therefore, should not be used for that diagnosis in most instances.

My support frame invention can be used effectively to produce relaxation with a positive effect on pain via gentle stretch in a flexed position combined with a mild traction of the weight bearing intervertebral joints for:

1. More effectively managing certain conditions with little or no intervention by a health care professional. In other words, as a home therapy program initially guided by a professional by prescription, or purchased by a lay person without prescription and without professional supervision.
2. It can be used by health care providers as a valuable, brief treatment immediately prior to other treatments in the clinic, such as before applying traction (with some exceptions), manipulation, mobilization and the like, to be more effective (indicated conditions would be almost always in the subacute and chronic phases) and unsupervised patient use as part of a home program.

Secondary benefits include further improvement in the relief of pain, release of hypomobile facet joints and costovertebral joints, and reduction of soft-tissue hypomobilities.

My support frame is unique in that it is a stand-alone floor design and combines gravity-assisted gentle, static traction (circumventing the TMJ) with mild flexion stretch of neck and upper back posterior soft-tissue components.

My support frame also has value in the clinic in connection with a brief, preparatory treatment in both subacute and chronic therapy regimes for the neck and upper back, enhancing effectiveness of subsequent techniques by its relaxation effects. Once instructed, the technician or therapist can perform the set-up or the patient may perform self-setup. Either way, employee time is minimized. And the physical strain to the professional while performing a manual technique is eliminated.

The professional prescribing my support frame for home use is likely to see good follow-through in patient compliance as a result of its comfort and ease-of-use.

My support frame invention is intended for use by the following: the unsupervised at-home patient; physical therapist; D.O.; massage therapist; and D.O.C. in connection with therapy for relieving pain conditions of the neck and upper back including general aches and pains, tension or muscle spasm, tension headache, facet joint subluxation (hypomobility), soft tissue hypomobility, degenerative disc disease, other joint disorders, including some classifications of arthritis.

Although the invention has been described with reference to an exemplary arrangement, it is to be understood that various changes, substitutions and modifications can be realized without departing from the spirit and scope of the invention as defined by the appended claims.

TABLE I

| Description | Material |
|---|---|
| Bolster Board 16 | High impact polystyrene (HIPS) injection molded |
| Base Platform 14 | High impact polystyrene (HIPS) injection molded |
| Head Cradle 18 | ABS plastic, injection molded |

TABLE I-continued

| Description | Material |
|---|---|
| Covering 76 | Vinyl; foam padding |
| Strap 70 | Nylon |
| Upper Cross-Bar 50 | Aluminum tubing, 1" O.D. |
| Lower Cross-Bar Assembly 28 | Aluminum tubing, 1" O.D. |
| Left and Right Base Rails 14A, 14B | Square tubing, aluminum (1" × 1" × .062" wall) |
| Left and Right Struts 40, 42 | Square tubing, aluminum (1" × 1" × .062" wall) |
| Pivot Assembly 44, 46 | Machined steel |
| Swivel Assembly 48 | Machined steel |
| Non-Skid Pad 72, 74 | Synthetic rubber |

What is claimed is:

1. A portable frame for supporting passive cervical traction during the administration of physical therapy comprising, in combination:

a support platform for placement onto a treatment surface;

a head support frame including a first end portion pivotally coupled to the support platform for movement from a collapsed position to an upright treatment position in which the head support frame projects transversely with respect to the base support platform;

a head cradle mounted on the head support frame;

a strut assembly including first and second struts coupled to the head support frame and to the support platform for maintaining the head support frame in the upright treatment position;

the base support platform including a first cross bar having first and second end portions pivotally coupled to the first and second base rails, respectively;

the strut assembly including a second cross bar, the second cross bar having first and second end portions pivotally coupled to the first and second struts, respectively; and, the head support frame including opposite end portions that are pivotally coupled to the first and second cross bars, respectively.

2. A portable support frame as set forth in claim 1, wherein:

the head support frame including a bolster board, the bolster board being intersected by a pair of index slots; and, the head cradle including a support plate disposed on the bolster board, and including first and second retainer hooks projecting from the support plate and received within the index slots.

3. A portable support frame as set forth in claim 1, wherein:

the head support frame including a bolster board, the bolster board being intersected by multiple pairs of index slots;

the head cradle including a coupling plate, the coupling plate being releasably attached to the bolster board; and, position adjustment apparatus attached to the coupling plate and engaged in a selected pair of the index slots for manually releasing the coupling plate from the bolster board and subsequently repositioning the head cradle at a different elevation position relative to the base platform.

4. A portable support frame as set forth in claim 3, wherein:

the position adjustment apparatus comprises a pair of L-shaped brackets projecting from the coupling plate, the L-shaped brackets being insertable into the index slots and engagable with the bolster board for fixing the elevation position of the head cradle relative to the base platform.

5. A portable support frame as set forth in claim 1, wherein:

the head cradle includes first and second occipital engagement portions, the engagement portions diverging with respect to each other and defining an included angle in the range of 90°–110°.

6. A portable support frame as set forth in claim 1, wherein:

the head support frame is inclined at an angle in the range of 75°–90° with respect to the base platform when the head support frame is in the upright treatment position.

* * * * *